United States Patent [19]

Potts

[11] 4,226,230

[45] Oct. 7, 1980

[54] ORTHOPEDIC DEVICES, MATERIALS AND METHODS

[75] Inventor: James E. Potts, Millington, N.J.

[73] Assignee: Union Carbide Corporation, New York, N.Y.

[21] Appl. No.: 24,320

[22] Filed: Mar. 27, 1979

Related U.S. Application Data

[62] Division of Ser. No. 881,138, Feb. 24, 1978, abandoned.

[51] Int. Cl.$^3$ .............................................. A61F 5/04
[52] U.S. Cl. ..................................................... 128/90
[58] Field of Search ......................................... 128/90

[56] References Cited

U.S. PATENT DOCUMENTS

| 3,692,023 | 9/1972 | Phillips et al. | 128/90 |
| 4,019,505 | 4/1977 | Wartman | 128/90 |

FOREIGN PATENT DOCUMENTS 847404  2/1977  Belgium .

*Primary Examiner*—C. Fred Rosenbaum

*Attorney, Agent, or Firm*—Bernard Francis Crowe

[57] ABSTRACT

There are provided orthopedic casts, splints, and the like, for use on a portion of a human or animal body, which are produced from a crosslinked copolymer of a lactone monomer and a polyfunctional acrylate monomer. The crosslinked copolymer, in the form of a sheet, web, bandage, etc., and, optionally, a supportive substrate, is heated above the softening point of the copolymer, manipulated to conform to the body portion, and cooled to a rigid state.

In one embodiment, there is provided a bandage material, convertible to a rigid, porous, light-weight orthopedic cast, which comprises a substrate in the form of a netting, having on the surfaces of its strands a coating of the aforementioned crosslinked copolymer. The bandage material is heated to a temperature at which the crosslinked copolymer is soft and self-adherent and is then wrapped around the body portion in a series of overlying layers so as to conform to the contours of the body portion. The overlying layers are fused together to form a close-fitting unitary cast and are then cooled to a rigid state.

8 Claims, 2 Drawing Figures

ORTHOPEDIC DEVICES, MATERIALS AND METHODS

This is a division of Ser. No. 881,138 filed Feb. 24, 1978 and now abandoned.

BACKGROUND OF THE INVENTION

1. Field of Invention

This invention relates to orthopedic devices such as casts, splints, and the like; to materials and methods for making same; and to methods of producing certain of the materials which are used in their fabrication. The orthopedic casts, splints and the like are useful in the treatment of the animal or human body for the maintenance of immobilization and fixation following reduction of fractures and dislocations, the maintenance of approximation of bone fragments following reduction of fractures, the maintenance of immobilization and fixation to promote healing in instances of compound fractures and bone disease, the immobilization of inflamed or injured joints in disease or trauma, and the support and immobilization of ligamentous and muscular structures in instances of sprains and strains. The orthopedic devices provided by this invention may also be used as an occlusive dressing for wounds of the extremities by encasing the limb or part to reduce motion and accelerate healing; as a support splint in paralysis or weakness of muscles; and as a means to maintain correction of deformities; either congenital or acquired. They may also be used as a means of protecting or supporting limbs or other body parts during athletic activities and the like.

As used herein the term "orthopedic device" is intended to include devices externally applied to a portion of the human or animal body for any of the above purposes, regardless of whether they may be otherwise categorized as casts, splints, supports, braces, shields, body casts, etc. Specifically excluded from its meaning are devices intended to be surgically implanted in the body, such as bone implants.

2. Description of the Prior Art

Plaster of Paris has long been widely used as a material for fabricating orthopedic casts. Unfortunately, casts made of this material are heavy, bulky, sensitive to water, brittle and relatively easily broken, so that casting may have to be repeated. Moreover, they are difficult to clean and are not soil-resistant, they lack transparency, and have relatively poor x-ray penetrability. They are not very permeable to moisture and thereby tend to trap perspiration, creating a medium for the buildup of bacteria and offensive odors.

In attempting to overcome the problems associated with plaster casts, a number of plastic materials have been employed in orthopedic devices. For example, in U.S. Pat. No. 2,616,418 specific crystalline non-polymeric organic compounds having sharp melting points between 45° C. and 100° C. are admixed with specific high molecular weight thermoplastic substances, such as cellulose acetate, to form cast-forming compositions. U.S. Pat. No. 2,385,879 discloses a plastic cast material comprising a particular plasticizer and a conjoint polymer of a vinyl ester of an aliphatic acid and a vinyl halide. U.S. Pat. No. 3,420,231 discloses a thermoplastic cast forming material that is flexible and moldable at about 165° F. The sheet contains a fibrous substrate coated with a cast forming material comprising a specific elastomeric type resin, such as trans 1,4-chloroprene polymer and a specific inversely soluble resin, such as methyl cellulose or polyvinyl methyl ether.

U.S. Pat. No. 3,692,023 describes orthopedic casts, splints, and the like which are produced from supported or unsupported webs or sheets of cyclic ester polymers, such as poly-epsilon-caprolactone. Orthopedic casts made from this material display excellent properties and have solved a number of problems exhibited by the various other plastic casts of the prior art. These casts are rigid, non-irritating, strong, durable, water-resistant, and soil-resistant. Further, they are easily removed and can be sterilized and reused. There is no danger of skin irritation due to components, such as plasticizers, separating from the polymer and exuding out of the cast.

Yet, despite the ingenuity displayed in the prior art and the advances which have been made, there are still unsolved problems in the field of orthopedic devices, and particularly in the area of plastic orthopedic devices. Plastic materials generally must be heated above their softening points in order to be applied to the body portion being treated. Some plastic materials, such as the cyclic ester polymers employed in U.S. Pat. No. 3,692,023, are characterized by well defined melting points, above which the melt index rises sharply. In applying such materials such as orthopedic casts, they tend to be more fluid at the application temperature than would be desired by the practitioner and, thus, somewhat difficult to handle. Other polymeric materials which have been employed in orthopedic devices have softening or melting points at temperatures which are too high to be comfortably applied to the patient. Ideally, a polymeric material to be used in orthopedic devices should be one which becomes soft and malleable, but not highly fluid, at a temperature which is above room temperature, yet not so high as to cause the patient discomfort during application.

In applying orthopedic casts, practitioners of orthopedic medicine generally prefer to use the cast material in the form of a bandage which can be wrapped around the body portion in overlying layers in order to provide a close conforming fit to the body portion. Orthopedic cast forming materials have been produced in the form of rolled bandages comprising a substrate, such as cotton gauze, having a polymeric coating or impregnation thereon. The roll of bandage material is heated, for example by immersing it in a hot water bath, until the temperature of the polymer reaches its softening point, and the cast is applied by wrapping the heated bandage around the limb or other body part as it is drawn off the roll. A number of problems have occurred when attempting to apply casts in this manner using the prior art known plastic cast forming materials. Due to relatively high melt index at the application temperature and/or high degree of self-adhesion of the polymer, it is frequently necessary to insert a release-coated separating sheet between the layers of the rolled bandage to prevent the layers from fusing or sticking together on the roll when the roll is heated. Further, the outer layers of the rolled bandage tend to insulate the inner layers, resulting in uneven heating. Consequently, the outer layers may be too hot for the comfort of the patient or the inner layers may not be sufficiently heated to allow the practitioner sufficient working time to apply the cast. Although hot water is the most widely used medium for heating plastic orthopedic cast forming bandages, the high heat capacity of the water can result in discomfort to the patient at the relatively high temperatures needed to soften many of the known plastic cast forming materials.

SUMMARY OF THE INVENTION

This invention provides improved orthopedic devices and methods and materials for their manufacture. An essential feature of the orthopedic devices of this invention is that they are made using a crosslinked copolymer of a lactone monomer and a polyfunctional acrylate monomer. The precursor from which the crosslinked copolymer is produced is a thermoplastic, crosslinkable copolymer of the lactone monomer and polyfunctional acrylate. The thermoplastic, crosslinkable copolymer is the subject of our copending patent application Ser. No. 880,955, now U.S. Pat. No. 4,175,177, the disclosures of which are incorporated herein, and is described in greater detail therein. The thermoplastic, crosslinkable copolymer can be conveniently crosslinked by exposure to radiation, such as electron beam or ultraviolet radiation, or by the known chemical crosslinking agents such as peroxides.

By comparison with the plastic cast forming materials known in the prior art, the crosslinked copolymers employed herein have a number of important advantages. By controlling the degree of crosslinking in the copolymer, one can control the rheological and other properties of the material to provide optimum properties for applying them to the body portion being treated. Unlike the cyclic ester homopolymers used in U.S. Pat. No. 3,692,023 and certain other polymers, the crosslinked copolymers used herein do not become fluid upon heating, but rather, become soft and rubbery. In this condition they are very easily manipulated about the body portion and retain the desired shape upon cooling. The onset of this soft, rubber behavior (hereinafter referred to as the "softening point") occurs in the range of from about 40° C. to about 70° C. While the heated material is sufficiently self-adherent that it can be fused into a unitary cast by the practitioner applying it to the body portion, its adhesion and rheological properties are controllable such that the material can be produced in the form of a rolled bandage without the necessity of a separating sheet between the layers. The rolled bandage can be heated to the softening point of the crosslinked copolymer without danger that the layers will irreversibly fuse or stick together on the roll.

Generally, the orthopedic devices of this invention can be produced from cast forming materials of the crosslinked copolymer in the form of sheets, tapes, films, webs, bandages, preformed contour fitting shapes, etc., which can be bonded to or have impregnated therein supportive substrates. The particular form of the crosslinked copolymer used will depend largely on the nature of the orthopedic device being produced.

In one embodiment of the invention, there is provided a bandage material, convertible to a rigid, porous, lightweight orthopedic cast, which comprises a substrate in the form of a netting, the strands of said netting having on their surfaces a coating comprising the crosslinked copolymer. The bandage material is heated to a temperature above the softening point of the copolymer and is then wrapped around the body portion in a series of overlying layers to form a cast conforming to the contours of the body portion. The heated layers of the applied bandage are easily fused into a unitary structure by the slight application of pressure to ensure surface contact between the layers. The cast thus formed contains myriad passages through which air and moisture can pass, yet it is sufficiently rigid and strong to be used in load-bearing applications such as lower leg casts.

Another advantage of the crosslinked copolymers employed in this invention is that their dielectric characteristics are such that they can be conveniently heated by exposure to electromagnetic wave energy in the microwave region. Thus, a rolled bandage material, such as that described above, can be placed in a microwave oven and heated rapidly without the use of a hot water bath. The microwave energy has the advantage of penetrating to the interior layers of the rolled bandage to provide even heating. Since the inner layers of rolled bandage are somewhat insulated by the outer layers, they maintain their temperature sufficiently to provide the practitioner with an adequate working time for application of the cast. Moreover, since this method employs "dry" heating, there is less chance of discomfort to the patient.

DETAILED DESCRIPTION OF THE INVENTION

Figure 2:
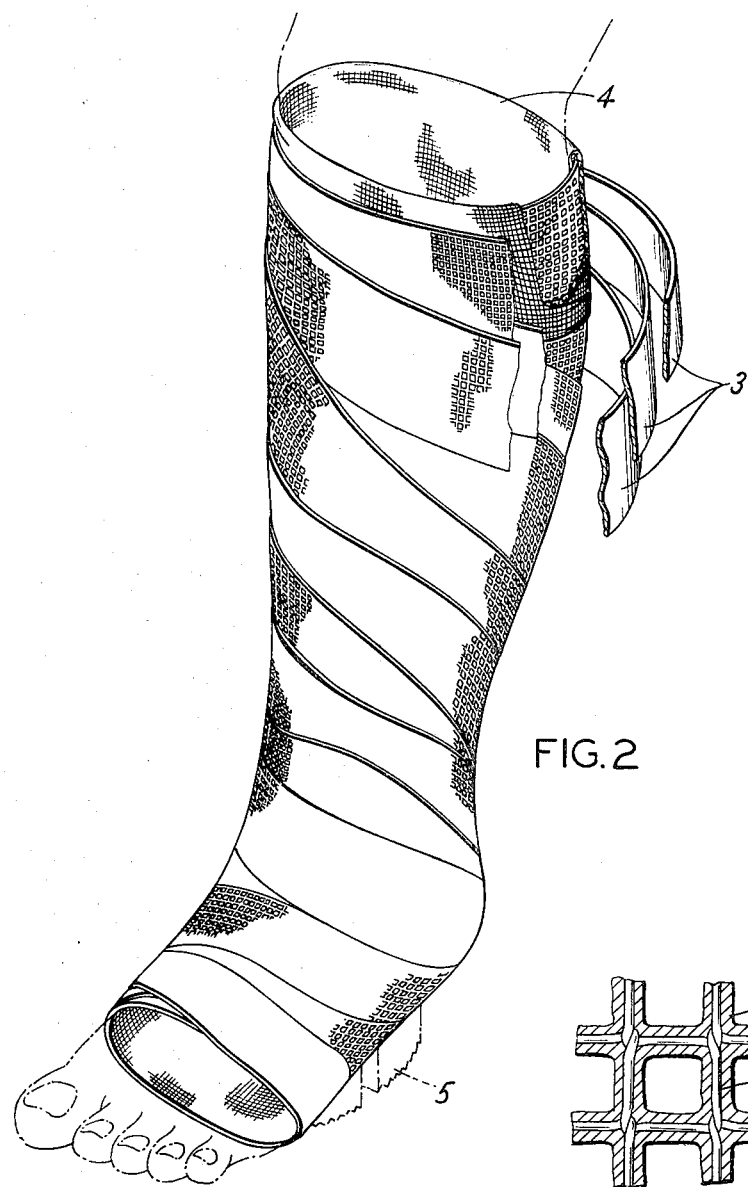
FIG. 2 is a perspective drawing of a lower leg cast produced in accordance with the teachings of this invention from an orthopedic cast forming bandage in the form of a coated netting. A portion of the cast is shown as a cross-section showing the individual layers of bandage material separated from each other.

The orthopedic devices of this invention employ, as a material of construction, a crosslinked copolymer which is produced from a thermoplastic, crosslinkable copolymer precursor. The crosslinked copolymer can contain a gel content of up to about 90 weight percent (measured as weight percent of the copolymer which is insoluble in methylene dichloride). Preferably, it contains a gel content from about 20 to 70 weight percent.

The thermoplastic, crosslinkable copolymer which is the precursor of the crosslinked copolymer used in this invention is produced by reacting, at a temperature of from about 25° to 300° C., an active-hydrogen containing initiator with a molar excess of a monomer mixing comprising:

(A) from 90 to 99.5 weight percent, preferably from 95 to 99.5 weight percent, of at least one lactone of the formula

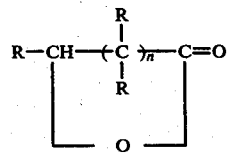

wherein n is an integer having a value of from about 3 to 6, at least n+2 of the R's are hydrogen and the remaining R's are alkyl of 1 to 10 carbons; and (B) from 0.5 to 10 weight percent, preferably from 0.5 to 5 weight percent, of a polyfunctional acrylate.

As used in this specification and claims, the term "polyfunctional acrylate" means any of the di-, tri-, or tetrafunctional acrylate or methacrylate esters defined by the formula

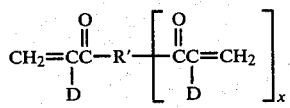

wherein each D is hydrogen or methyl, x has a value of 1 to 3, R' is

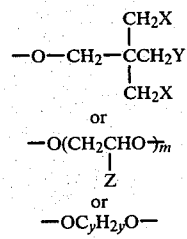

wherein X is hydrogen or —O—, Y is —O—, methyl, or

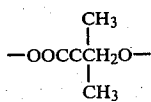

Z is hydrogen or alkyl of 1 to 2 carbon atoms, m has a value from 2 to 6, and y has a value of from 2 to 15.

One can mention, as illustrative of the polyfunctional acrylates described above, neopentyl glycol diacrylate, neopentyl glycol dimethyacrylate, trimethylolpropane triacrylate, trimethylolpropane trimethacrylate, butanediol diacrylate, butanediol dimethacrylate, 3'-acryloxy-2',2'-dimethylpropyl 3-acryloxy2,2-dimethyl-propionate, ethylene glycol diacrylate, diethylene glycol diacrylate, pentaerythritol triacrylate, pentaerythritol trimethacrylate, pentaerythritol tetracrylate, and the like.

It will be appreciated that, in producing the polyfunctional acrylates by esterifying the corresponding polyfunctional alcohols, some residual hydroxyl groups may be present in the product. A small amount of such residual hydroxyl groups is tolerable in producing the thermoplastic, crosslinkable copolymers, however, they will act as active-hydrogen initiators and their effect on molecular weight should be taken into consideration.

Illustrative of the lactone monomers described above, one can mention epsilon-caprolactone, zeta-enantholactone, delta-valerolactone, the monoalkyl-delta-valerolactones, e.g. the monomethyl-, monoethyl-, monohexyl-delta-valerolactones, and the like; the monalkyl-, dialkyl-, and trialkyl-epsilon-caprolactones, e.g. the monomethyl-, monoethyl-, monohexyl-, dimethyl-, diethyl-, di-n-propyl-, di-n-hexyl-, trimethyl-, triethyl-, tri-n-propyl-epsilon-caprolactones, and the like.

The identity of the active-hydrogen containing initiators and the reaction conditions which promote the copolymerization of the lactone and polyfunctional acrylate, including the nature of useful catalysts, are essentially the same as those known to promote the polymerization of the lactone monomer alone. The polymerization of lactone monomers with active-hydrogen containing initiators is known in the art and is described in U.S. Pat. No. 3,169,945.

The active-hydrogen containing initiators which are useful in producing the thermoplastic, crosslinkable copolymers are known to those skilled in the art. They are compounds having one or more reactive hydrogen atoms which are capable, under the conditions of reaction, of opening the lactone ring and adding it as an open chain without forming water of condensation. Suitable initiators include the monofunctional initiators such as water, alcohols, and amines and the polyfunctional initiators such as the polyols and polyamines, as well as amides, sulfonamides, hydrozones, semicarbazones, oximes, polycarboxylic acids, hydrocarboxylic acids, and aminocarboxylic acids.

As merely illustrative of suitable active-hydrogen initiators one can mention: alcohols such as methanol, ethanol, propanol, isopropanol, 1-butanol, 2-butanol, tert-butanol, 1-pentanol, 3-pentanol, tert-amyl alcohol, 1-hexanol, 4-methyl-3-pentanol, 1-heptanol, 1-octanol, 1-nonanol, 2,6-dimethyl-4-heptanol, 5-ethyl-2-nonanol, 3,9-triethyl-6-decanol, lauryl alcohol, benzyl alcohol, phenyl methyl carbinol, cyclohexanol, and trimethylcyclohexanol; diols such as ethylene glycol, diethylene glycol, triethylene glycol, and the like, 2,2-dimethyl-1,3-propanediol, 2,2-diethyl-1,3-propanediol, 3-methyl-1,5-pentanediol, N-methyl and N-ethyl diethanolamines, 1,3- or 1,4-cyclohexanediol, 4,4-methylenebiscyclohexanediol, 1,3- or 1,4-xylenediol, 3- or 4-hydroxymethylphenethyl alcohol, and 1,4-piperazinediethanol; amines such as methylamine, ethylamine, n-propylamine, isopropylamine, n-butylamine, tert-butylamine, n-amylamine, n-hexylamine, 2-ethylhexylamine, aniline, orthotoluene, cyclohexylamine, pyrrolidone, piperidine, and morpholine; and diamines such as methylenediamine, ethylenediamine, n-propylenediamine, meta- or para-phenylenediamine, toluene-2,4-diamine, 1,5-napththalenediamine, meta- or para-xyxlyenediamine, 1,4-cyclohexanediamine, and 4,4'-methylenebiscyclohexylamine.

The above listing of suitable active-hydrogen containing initiators is intended to be illustrative only and not to be an exhaustive listing. A more complete listing of active-hydrogen containing initiators which can be used in the production of the thermoplastic, crosslinkable copolymer is found in U.S. Pat. No. 3,169,945, Cols. 2-7.

Those skilled in the art will be aware that the molar ratio of monomers to initiator and the functionality of the initiator are major factors affecting the molecular weight of the resultant polymers. For purposes of employing the resultant copolymers in the production of the orthopedic devices of this invention, it is preferred that the thermoplastic, crosslinkable copolymer precursor have a reduced viscosity of from about 0.2 to 2.0, preferably 0.5 to 1.0, at a concentration of 2 grams/ml in benzene.

The polymerization of the lactone and the polyfunctional acrylate is preferably carried out in the presence of a lactone polymerization catalyst, such as a basic or neutral ester interchange catalyst. Among catalysts suitable for this purpose are such metals as lithium, sodium, potassium, rubidium, cesium magnesium, calcium, barium, strontium, zinc, aluminum, titanium, cobalt, germanium, tin, lead, antimony, arsenic, and cerium, as well as the alkoxides thereof. Additional suitable catalysts, by way of example, are the carbonates of alkali- and alkaline earth, zinc borate, lead borate, zinc oxide, lead silicate, lead arsenate, litharge, lead carbonate, antimony trioxide, germanium dioxide, cerium trioxide, cobaltous acetate, and aluminum isopropoxide. The catalysts are employed in the usual known catalytically effective concentrations. Typically, the catalysts are employed at concentrations between about 0.001 to 0.5%, preferably from 0.01 to 0.2%, based on the weight of the lactone monomer.

The reaction of the lactone, polyfunctional acrylate, and active-hydrogen containing initiator is carried out at a temperature from 25 to 300° C., preferably from 130° to 225° C. Reaction time varies widely, depending on the type and amount of initiator lactone, polyfunctional acrylate, and catalyst, reaction temperature, desired molecular weight, etc. and can be anywhere from a few minutes to 40 hours or more. The product is recovered by conventional means.

While not wishing to be bound by a particular theory of structure or mechanism, it is believed that the thermoplastic crosslinkable copolymer comprises a polylactone backbone containing the residue of the initiator therein and having the polyfunctional acrylate units grafted thereto. Analysis of the double bond content of the copolymer indicated that approximately half the double bonds of the starting polyfunctional acrylate were consumed in the polymerization reaction when neopentyl glycol diacrylate was copolymerized with epsiloncaprolactone.

The degree to which the crosslinked copolymer softens or flows at a given temperature near or above the crystalline melting point depends upon the degree of crosslinking. Thus, if one desires a higher degree of flow or softness in the cast forming material at the application temperature, a lower degree of crosslinking can be employed. The degree of crosslinking also affects other properties of the crosslinked copolymer such as its adhesion to itself and to other materials, its tensile strength in the melt, and its resistance to deformation at elevated temperatures.

In producing the orthopedic devices, the crosslinked copolymers are used in the form of sheets, webs, and the like, which can have continuous or foraminous surfaces. As will be evident from the discussion below, the sheets or webs can range in thickness from those which are relatively thick and are applied to the body portion in a single-layer thickness to those which are relatively thin and are applied in a series of overlying layers to build up the necessary thickness to give the desired degree of support, immobilization, and protection.

The copolymer can be crosslinked either prior to or subsequent to converting the copolymer to sheet form, or it can be partially crosslinked to the desired level prior to converting it to a sheet form and the sheet can then be further irradiated. It should be kept i mind, however, that too high a degree of crosslinking in the copolymer may render the copolymer unprocessable by conventional thermoplastic processing techniques used to produce sheet stock, e.g. extrusion.

The sheet stock can be produced by extruding the thermoplastic, crosslinkable copolymer into a sheet and then irradiating the sheet, for example, with electron beam, gamma-rays, x-rays, alpha-rays, beta-rays, ultraviolet light, etc., to crosslink the copolymer to the desired extent.

If one desires to crosslink the copolymer by exposure to radiation of a non-ionizing type, e.g. ultraviolet light, then it is preferred to have blended into the copolymer a photoinitiator. Any of the known photoinitiators can be employed. As merely illustrative thereof, one can mention 2,2-diethoxyacetophenone, 2,2-dimethoyoxyphenoxyacetophenone, 2- or 3- or 4-bromoacteophenone, 3- or 4-bromoacetophenone, 3- or 4-allylacetophenone, 2-acetonaphthone, benzaldehyde, benzoin, the allyl benzoin ethers, benzophenone, benzoquinone, 1-chloroanthraquinone, p-diacetyl-benzene, Michler's Ketone, p-methoxybenzophenone, dibenzosuberone, 4,4-dichlorobenzophenone, 1,3-diphenyl-2-propanone, fluorenone, 1,4-napthyl-phenylketone, 2,3-pentanedione, propiophenone, chlorothioxanthone, 2-methylthioxanthone xanthone and the like, or any mixtures of these. The photoinitiators, when present, are at the usual known effective concentrations, typically up to about 10 weight percent, preferably from 1 to 5 weight percent, based on the weight of the thermoplastic, crosslinkable copolymer.

The crosslinked copolymers can also contain up to about 20 weight percent, based on the weight of the copolymer, of particulate or fibrous fillers, such as reinforcing fillers, e.g. magnesium or calcium carbonate, finely divided silica, clay, asbestos, glass fibers, etc., or pigments, e.g. titanium dioxide. Dyes or other coloring agents may also be present in suitable concentrations if one desires to produce the orthopedic device in a particular color.

The crosslinked copolymer in sheet form can have a substrate, in the form of a sheet or web of a different material, bonded to the surface thereof or embedded therein, or the crosslinked copolymer can be impregnated into or coated onto the substrate.

The substrate material can be employed as a supportive substrate or as a soft backing layer disposed between the crosslinked copolymer and the skin of the wearer to act as a cushion. Preferably, the substrate material is one which is flexible and which is solid at temperatures up to 80° C. or higher.

If desired, a conventional fabric stockinette can be placed over the body portion prior to applying the orthopedic device.

As merely illustrative of suitable substrates for such purposes one can mention:

(a) fabrics or nettings of synthetic or natural materials which can have continuous or foraminous surfaces. Included therein are cellulosic fabrics such as flannel or gauze made from cotton; rayon; blends of cotton or rayon; blends of cotton or rayon with synthetic fibers such as poly(ethylene terephthalate), polyacrylonitrile, nylon, polyester, polyethylene, and polypropylene fibers, and the like; and glass fiber cloth;

(b) non-porous sheets or webs of polymers such as extruded, cast, or calendared sheets of: cellulose derivatives, for example, nitrocellulose, solid cellulose ethers including ethyl cellulose, methyl cellulose, hydroxy ethyl cellulose, carboxy methyl cellulose, cellulose esters such as cellulose acetate, and the like; nylons; thermoplastic polyurethanes; polyesters of polycarboxylic acids and polyhydric alcohols; the normally solid acrylic polymers and copolymers, such as poly(methyl methacrylate), poly(ethyl methacrylate) and the like; elastomers such as natural rubber and synthetic rubbers, including butyl rubber, polybutadiene rubber, polyisobutylene rubber, acrylonitrile-butadiene-styrene rubbers, and silicone rubbers; and (c) flexible foams such as polyurethane foam, foam rubber, or natural sponge.

The orthopedic devices of this invention can be produced by either of two basic methods. In the first method, a single sheet, having the thickness desired in the applied orthopedic device, is heated to a temperature above the softening point of the crosslinked polymer and the softened sheet is manipulated to conform to the surface contour of the body portion to which it is applied. If the orthopedic device being formed is of the type which completely encases the body portion being treated, i.e. a cast, then the edges of the heated sheet are brought together in overlapping or abutting fashion and fused, by the application of pressure if necessary. The applied sheet is then cooled to a rigid state. This first method is particularly well suited to the formation of splints, braces, and the like, which support and immobilize the body portion but which do not necessarily form an encasement for the body portion in the manner of a cast. Any suitable fastening means can be employed to affix such devices to the body portion. Typically, a bandage can be wrapped around the orthopedic device, e.g. a splint, and the body portion to which the device is applied, e.g. an arm or leg, and held in place by means of pins, clips, etc. The orthopedic device can also be held in place by means of so-called "velcro" fasteners, which can be embedded in or affixed to the surface of the splint, brace, etc. It is preferred that the sheet employed in this first method have a thickness of at least $\frac{1}{8}$ inch to provide sufficient immobilization, support, and protection, however, a somewhat thinner sheet may be used in conjunction with a supportive substrate or reinforcing filler. It can have a thickness of up to about $\frac{1}{2}$ inch or more, if desired.

The second basic method of producing orthopedic devices from the crosslinked copolymer employs the crosslinked copolymer in the form of a relatively thin sheet, or bandage. This method is preferred in applications such as casts which are applied following the reduction of fractures, wherein it is necessary that the orthopedic device form an encasement for the body portion which conforms very closely to the contours of the body portion, to prevent even slight movement during healing. In this method, the sheet or bandage is heated to a temperature above the softening point of the crosslinked copolymer and is then wrapped around the body portion in a series of overlying layers conforming to the surface contours of the body portion to build up a sufficient thickness of material to provide rigidity at room temperature. Each layer is fused to the layers beneath and above it, by the slight application of pressure if necessary to assure adequate surface contact between the layers; and the cast thus formed is allowed to cool to form a unitary, rigid structure.

The sheet or bandage which is employed in the second method described above can have a thickness from about 10 mils to 125 mils. It can consist solely of a sheet of the crosslinked copolymer, which can be continuous or foraminous. Alternatively, the crosslinked copolymer can be bonded to or coated onto or have embedded therein a thin web or sheet of a different material as a substrate. Any of the previously mentioned substrate materials are useful for this purpose.

A suitable bandage for this purpose can be produced by coating a substrate with a powder of the thermoplastic crosslinkable copolymer, fusing the thermoplastic crosslinkable copolymer to the substrate by the application of heat, cooling the bandage material, and then crosslinking the copolymer on the bandage under an electron beam or ultraviolet light source. Alternatively, the thermoplastic, crosslinkable copolymer can be bonded to the substrate by extrusion coating or by casting a film of the thermoplastic crosslinkable copolymer onto the substrate, or by dipping the substrate in or spraying the substrate with an organic solvent solution of the copolymer and evaporating the solvent. The copolymer is then crosslinked.

In a preferred embodiment of the invention, orthopedic casts are produced from a bandage material comprising a substrate in the form of a netting, the strands of said netting having on their surfaces a coating comprising crosslinked copolymer. The netting can be knitted or woven, a knitted netting being preferred because it exhibits a somewhat greater degree of dimensional stability.

Figure 1:
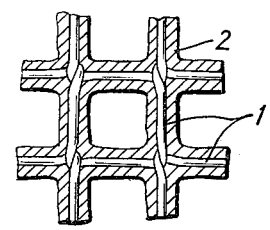
FIG. 1 is a cross-sectional view of an orthopedic cast forming material in the form of a coated netting.

FIG. 1 illustrates a cross section of a cast forming bandage wherein the strands of the netting, 1*, have the crosslinked copolymer coating, 2*, on their surfaces. The thickness of applied coating on each strand can vary, being generally greater for netting having larger spacing between strands. Preferably, the coating thickness should not be so great that it "bridges" or closes the spaces between strands.

The cast forming bandage in the form of the netting having the coating of crosslinked copolymer on its surface is converted to an orthopedic cast by the process previously described; that is, the bandage is heated above the softening point of the crosslinked copolymer; the heated bandage is wrapped about the body portion in a series of overlying layers to form an encasement for the body portion which conforms to the surface contours thereof; the overlying layers are fused together; and the cast is cooled to a rigid state. Since the openings between the strands in each layer are randomly aligned with those of the layers above and below it, a cast is formed which has myriad random passages through which air and moisture can pass. The cast is lightweight, yet strong. The applied cast forms a close-fitting, custom contoured structure which completely encases the body portion being treated except, of course, that there are openings suitably disposed in the surface thereof to allow for the protrusion of connected body parts not being treated, e.g. fingers, toes, etc.

FIG. 2 illustrates a typical cast, i.e. a leg cast, produced from the bandage using the net substrate. A portion of the figure is broken away to show the cast construction. In the broken section the several overlying layers of bandage, 3, are shown peeled away from each other, although it is to be understood that the layers are fused to each other in the actual cast. A fabric stockinette, 4, can be placed on the leg prior to applying the first bandage layer and folded over the first bandage layer at the top. The next bandage layer is then applied over it to hold it in place. An conventional heel piece 5, can be affixed to the bottom of the cast if it is intended to be a walking cast. For convenience, only a portion of the cast surface has been drawn to show the fine network of strands and openings which actually cover the entire surface.

Each of the strands of the net substrate can comprise a single element, such as an extruded strand, or a plurality of fibers, which can be plaited, twisted, etc. to form a strand. It is preferred that the netting be flexible and any suitable natural or synthetic material may be employed, e.g., strands comprised of a plurality of natural fibers such as cotton or wool, or strands of synthetic material in the form of single strands or fibers, such as nylon, polyester, rayon, polyethylene, polypropylene, cellulose acetate, etc.

There is provided herein a convenient means of producing a bandage material from the net substrate which comprises: applying an electrically conductive coating to the surfaces of the strands of the netting and then electrostatically spray coating the strands of the netting with a powder of the thermoplastic, crosslinkable copolymer. The thermoplastic, crosslinkable copolymer coating which has been deposited on the strands of the netting is then crosslinked to the desired degree, for example, by exposure to electron beam radiation.

Those skilled in the art will recognize that electrostatic spray coating is a process wherein the object to be coated is electrically grounded and a spray of electrostatically charged powder particles is directed toward the object. The powder particles adhere to the grounded object and the object with the powder particles on its surface is heated to fuse the powder particles into a coating. The thermoplastic, crosslinkable copolymer can be reduced to powder form by cryogenically grinding the pellets. The suitable electrically conductive coatings which can be applied to the net substrate are well known and widely commercially available materials.

Other suitable methods of coating the substrate include fluidized bed powder coating or spraying the netting with a solution of the thermoplastic, crosslinkable copolymer in an organic solvent or with an aqueous emulsion of the thermoplastic, crosslinkable copolymer.

Preferably, the thermoplastic, crosslinkable copolymer coating is applied to the net substrate at a coating weight such that from 60 to 90 weight percent of the total bandage weight is copolymer.

As was previously mentioned, the crosslinked copolymer in the form of a sheet, web, bandage, etc., which is used to produce the orthopedic device of this invention can be conveniently heated, prior to application to the patient, by exposure to electromagnetic energy in the microwave region. Generally, the microwave region encompasses energy in the frequency range from about 500 to about 5,000 MHz. The crosslinked copolymers exhibit increasing absorption of microwave energy with increasing frequency in this range. Any of the well known types of equipment for generating microwave energy can be employed. Microwave ovens of the type commercially available for household cooking are suitable and convenient for this purpose, being tuned to operate at about 2,450 MHz.

Once applied to the patient, the orthopedic devices of this invention can easily be removed, for example, by heating and manipulating them away from the body. If the orthopedic device is comprised solely of the crosslinked copolymer and other organic polymeric materials, it can be removed by employing a hot wire or similar device to cut through the cast material. Of course, precautions must be taken to protect the patient from contact with the wire. Conventional cast cutters of the vibrating blade type, which are employed in the removal of plaster casts, are also suitable.

The examples which follow are intended to further illustrate the invention described above and are not intended to unduly limit the invention in any way. Unless otherwise stated, all parts and percents are given by weight.

The double bond contents of the copolymers were determined by the following procedure.

A small sample, in the order of 2 grams, was weighed into an Erlenmeyer flask, equipped with a condenser, into which there were also added 10 ml. of morpholine, 50 ml. of chloroform, and 20 ml. of acetic acid. The temperature of the contents was raised to about 50° C. for 30-45 min. to react the morpholine with the double bonds. The contents were then cooled to room temperature and titrated with 0.5 N perchloric acid in 2-methoxyethyl acetate to a thymol blue-xylene cyanol endpoint. A blank containing everything but the sample was also run. The double bond content was then calculated according to the equation $$\% \diagup C = C \diagdown = \frac{(A - B) \times N \times 0.01201}{S.W.} \times 100$$

A = ml. of perchloric acid to titrate sample
B = ml. of perchloric acid to titrate blank
N = normality of perchloric acid
S.W. = sample weight.

Reduced viscosities were determined at a concentration of 2 grams/ml. in benzene at 30° C.

EXAMPLE 1

To a 1-liter flask equipped with a thermometer, magnetic stirrer, nitrogen purge tube, and Brookfield viscometer there were charged 882 grams of epsilon-caprolactone (containing 0.024 wt.% water), 18 grams of neopentyl glycol diacrylate (containing 0.24 wt.% water), and 0.282 ml. of stannous octoate. Due to the water content of the reactants no additional initiator was necessary. The reactants were heated with a heating mantle to a temperature of 177° C. After two hours the temperature of the reactants had risen to 182° C. and the viscosity was 6,000 cps. After an additional two hours of reaction an exotherm was reached at 221° C. The reaction was continued for an additional five hours, at which time the product had a viscosity of 310,000 cps at 140° C. The viscous, yellowish product was discharged into a pan lined with silicone-coated release paper. The yield of solid polymer was 99.61% of the material charged. The polymer had a reduced viscosity of 0.58 in benzene at 30° C. and a double bond content of 0.11%.

The solidified polymer was removed from the release paper and granulated in a grinder. Samples of the granulated polymer were irradiated with varying dosages of electron beam energy using a 2 MEV electron accelerator. After irradiation the samples were tested for gel content in benzene, tetrahydrofuran, and methylene dichloride and rated for gel content on a scale of 0–6, with 0 representing no detectable gel and 6 representing the greatest amount of gel. Results appear in the table below.

| Radiation dose, megarads | $C_6H_6$ | $CH_2Cl_2$ | THF |
|---|---|---|---|
| 0 | 0 | 0 | 0 |
| 0.05 | 1 | 1 | 1 |
| 0.10 | 2 | 2 | 2 |
| 0.20 | 3 | 3 | 3 |
| 0.50 | 4 | 4 | 4 |
| 1.0 | 5 | 5 | 5 |
| 2.0 | 6 | 6 | 6 |

THF = tetrahydrofuran

EXAMPLE 2

A thermoplastic crosslinkable copolymer of epsilon-caprolactone and neopentyl glycol diacrylate was prepared by a procedure similar to that of Example 1, except that the reactants contained less water than those of Example 1. The reaction was carried out for about 9 hours, with an exotherm of 212° C. occurring after 4 hours, 15 min. After 9 hours the material had a viscosity of 740,000 cps at 130° C. The polymer was discharged onto silicone-coated release paper and cooled to room temperature. Yield of solid polymer was 99.3% and the polymer had a double bond content of 0.11%. Due to the lower amount of water used to initiate the reaction, the polymer in this example had a somewhat higher molecular weight than the polymer of Example 1, as indicated by a reduced viscosity in benzene of 0.72. Plaques ⅛-in. thick were compression molded from a portion of the thermoplastic crosslinkable copolymer. Some of the plaques were subjected to tensile testing. As a control, a conventional poly-epsilon-caprolactone homopolymer having a reduced viscosity of 0.95 was similarly tested and the results appear in the table below. Samples of the crosslinkable copolymer granules were irradiated with varying dosages of electron beam radiation and tested for gel content in methylene dichloride. The gel content was observed to increase with increasing radiation dosage, as in Example 1.

| | Secant modulus, p.s.i. | Tensile strength, p.s.i. at Yield | Tensile strength, p.s.i. at Break | Elongation % at Yield | Elongation % at Break |
|---|---|---|---|---|---|
| PCL | 35,900 | 1,850 | 4,000 | 15 | 280 |
| Copolymer | 43,500 | 2,150 | 3,300 | 13 | 380 |

EXAMPLE 3

In this example, a thermoplastic crosslinkable copolymer of this invention was produced in a 350-gallon jacketed reactor. There were charged to the reactor 1,500 lbs. of epsilon-caprolactone, 30 lbs. of neopentyl glycol diacrylate, 0.6 lbs. of stannous octoate, and 1.5 lbs. of diethylene glycol as initiator. The temperature of the reaction mixture was adiabiatically raised to 150° C. to start the reaction. The reaction was carried out for 15 hours, with two exotherms of 207° C. and 216° C. occurring after 1 hour and 1½ hours. The product was discharged in strands onto a cooled conveyor belt and the solidified strands were diced to form pellets. The product had a reduced viscosity of 0.54, a melt viscosity of 42,000 cps. at 200° C. and a double bond content of 0.11%. A portion of the polymer pellets were compression molded into 10-mil thick plaques, which were irradiated with 1 megarad of electron beam energy from a 2 MEV electron accelerator. A portion of one of the plaques was placed in methylene dichloride and formed a substantial amount of insoluble gel. By comparison, a portion of the unirradiated copolymer dissolved completely in methylene chloride.

Example 4

A portion of the thermoplastic, crosslinkable copolymer produced in Example 2 and a portion of the thermoplastic, crosslinkable copolymer produced in Example 3 were each compression molded into a number of plaques of ⅛-inch thickness. The plaques were irradiated with 2, 5, and 10 megarads of electron beam energy from a 2 MEV electron accelerator. Finger splints were then formed from the irradiated plaques, as well as from plaques which had not been irradiated. In forming the splints, the plaques were first placed in a hot water bath until the copolymers, which are opaque at room temperature, become translucent, indicating they had passed their crystalline melting points. The softened plaques were then wrapped around a finger in a tube-like manner, the edges were overlapped and fused together by the slight application of pressure, and the copolymers were allowed to cool to a rigid state. All of the irradiated copolymers were easily molded and fused, yet did not flow excessively or display dimensional instability during application. By comparison, the unirradiated plaques were rather fluid and difficult to handle during application. The applied splints held the fingers immobile.

Example 5

To a 350-gallon jacketed reactor there were charged 2,000 lbs. of epsilon-caprolactone, 40 lbs. of neopentyl glycol diacrylate, and 365 grams of stannous octoate. Trace water contained in the reaction mixture was the sole initiator employed. The temperature of the reactants was raised to 200° C. to start polymerization and the reaction was allowed to proceed for 15 hours. Prior to raising the temperature, a small sample of the reactant mixture was taken out of the reactor and placed in a thermocell. The reaction temperature in the thermocell was regulated to 200° C. and the reaction in the thermocell was allowed to proceed for 39 hours. The viscous, yellowish reaction product in the reaction was discharged in strands onto a cooled belt and the solidified strands were diced into pellets. A sample of the copolymer taken near the beginning of the reactor discharge had a reduced viscosity of 0.77 and a double bond content, in two repetitive measurements, of 0.09 and 0.08%. After 2 months this sample had a reduced viscosity of 0.74 and a crystallization time of 88 seconds. A sample of the copolymer taken near the end of the reactor discharge had a reduced viscosity of 0.81 and a double bond content, in two repetitive measurements, of 0.1 and 0.07%. After 2 months this sample had a reduced viscosity of 0.77 and a crystallization time of 77 seconds. The reaction product from the thermocell had a reduced viscosity of 0.89, double bond content, in two repetitive measurements, of 0.09 and 0.08%, and a crystallization time of 49 seconds.

Strips of knitted nylon netting, each 2 inches in width and 5 feet in length (86 strands per ft.) were mounted in a fume hood. The nylon netting used contained a melamine-formaldehyde size on its surface. The nylon netting was sprayed on both sides with a solution that was prepared by dissolving 10 weight percent of the copolymer produced above in methylene dichloride and then adding 10 weight percent titanium dioxide, based on the total weight of thermoplastic, crosslinkable copolymer. After drying overnight, the applied coating weight was 60–70 weight percent of the total weight of coated netting. The strips of coated netting were irradiated by exposure to 5 megarads of electron beam radiation from a 2 MEV electron accelerator. Using a Soxlet extractor, it was determined that a portion of the irradiated copolymer which had been removed from the netting had a gel content of 56.1 weight percent in methylene dichloride.

The irradiated strips of coated netting were employed as a cast forming bandage to form a lower leg cast. A cloth stockinette was placed over the lower leg and foot of the subject. The rolled bandages were placed in a 650-watt microwave oven (2,450 MHz) and heated to about 75° C., at which point the copolymer became soft and moldable but not highly fluid. The heated bandages were drawn off their rolls, with no sticking problems, and wrapped around the lower leg, ankle, and a portion of the foot in a series of overlying layers, taking tucks in the bandage wherever necessary, to form a close fitting cast and build up a sufficient thickness to provide rigidity, immobilization, and weight-bearing capacity at room temperature. The applied layers of bandage were fused together with the slight application of pressure to ensure good surface contact. The applied cast was allowed to cool to room temperature to solidify the copolymer. The applied cast was a rigid, unitary structure which was porous and permeable to the passage of air and moisture as a result of the openings in the layers of bandage.

A forearm-wrist cast was produced in a similar manner to the leg cast, wrapping the layers of heated bandage around the forearm and wrist, and passing between the thumb and forefinger, across the palm and thence back to the wrist.

A conventional lower leg cast made of a plaster impregnated casting tape weighed about 2.8 times the weight of the lower leg cast produced in the above described manner. A conventional forearm cast made from a plaster impregnated casting tape weighed about 5 times the weight of the forearm cast produced in the above described manner. The subject was able to walk on the lower leg cast made from the copolymer without bending or breaking the cast, indicating that there was adequate weight-bearing capacity in the cast material.

EXAMPLE 6

A strip of the nylon netting having the crosslinked copolymer coating on its strands, which was produced in Example 5, was heated to a temperature above the softening point of the copolymer. The heated material was fused to a strip of flexible polyurethane foam by the application of pressure. The heated, coated netting, bonded to the polyurethane foam, was wrapped around a forearm and wrist as the first layer of an orthopedic cast, with the polyurethane foam side in contact with the skin. Several layers of heated, coated netting materials, having no polyurethane foam bonded thereto, were then applied over the first layer to complete the cast, the layers fused together into a unitary structure, and the cast was allowed to cool to rigidify the copolymer. The cooled cast was rigid and conformed closely to the forearm and wrist. The polyurethane foam was a comfortable backing material and was found to have lower water retention time than the conventional fabric stockinette used in Example 5.

EXAMPLE 7

To a 350-gallon jacketed reactor there were charged 4,000 lb. of epsilon-caprolactone, 80 lb. of neopentyl glycol diacrylate, and 726 grams of stannous octoate. Trace amounts of water in the reactants were sufficient to act as a polymerization initiator. The temperature of the reactants was raised to 150° C. to start the reaction. The reaction proceeded for about 16 hours, with an exotherm of 224° C. occurring after about 5 hours. The viscous product was discharged in strands onto a cooled conveyor belt and the solidified strands were diced into pellets. The product had a reduced viscosity of 0.72.

Several 4-inch wide strips of knitted nylon netting, each 5 ft. in length (86 strands per ft.) were mounted in a fume hood. The nylon netting employed in this example had no sizing on its surface. A 10 weight percent solution of the copolymer produced above, in methylene dichloride, was prepared. There was added to the solution 10 weight percent titanium dioxide, based on the weight of the copolymer. The solution thus prepared was sprayed on both sides of the nylon netting mounted in the fume hood. After drying overnight, the applied coating weight was about 80 weight percent of the total weight of the coated netting. The copolymer on the netting was crosslinked by exposure to 3 megarads of electron beam energy from a 2 MEV electron accelerator. The gel content of the crosslinked copolymer on the netting was determined to be 54 weight percent, using a Soxlet extractor.

The strips of netting having the coating of crosslinked copolymer on their strands were employed as orthopedic cast forming bandages to form several lower leg casts and forearm casts on subjects in a manner similar to that employed in Example 5. Again, the casts formed were rigid, unitary and porous and permeable to moisture and air. The lower leg cast had adequate load-bearing capacity to allow the subject to walk on it.

During application to the subject, the bandage material of this example formed smoother, flatter tucks and fusion of the layers was somewhat more uniform and thorough than with the bandage material of Example 5. The lower degree of crosslinking (i.e. irradiation) and heavier applied coating weight employed in this example are believed responsible for the improved fusion by allowing the copolymer coating on the layers to achieve better contact and to flow together more readily. The lack of sizing on the nylon netting substrate allowed greater flexibility than the sized nylon substrate of Example 5, which is believed to be responsible for the improved tucking characteristics.

When the irradiation dosage used to crosslink the copolymer on similarly produced bandage material was about 2 megarads or lower, it was found that the tackiness and flow of the copolymer at the application temperature was such that a separating sheet would probably be necessary to prevent sticking between the layers of the rolled bandage.

EXAMPLE 8

To a food blender there were charged 900 grams of the thermoplastic, crosslinkable copolymer produced in Example 5, and 100 grams of titanium dioxide and the materials were physically blended for ½ hour. The mixture was then extrusion blended in a 1-inch screw diameter extruder. The material was discharged through a strand die into an ice bath to solidify the strands. The strands were diced into pellets, which were then cryogenically ground in a laboratory micropulverizer at −150° to −200° C. to produce a powder.

Several 2-inch wide strips of nylon netting, each 5 ft. in length (86 strands per ft.), were dipped in a solvent solution of an electrically conductive coating (supplied under the tradename Ransprep ®, Ransburg ElectroCoating Corp.) and the solvent was evaporated. The netting having the electrically conductive coating on its surface was electrostatically spray coated with the thermoplastic, crosslinkable copolymer powder. Applied coating weight was about 80 weight percent of the total weight of the coated netting. When the applied powder coating had been fused the openings between the strands of the coated substrate were still present; that is, the coating did not bridge or close the openings.

The netting having the thermoplastic crosslinkable copolymer on coating on its surfaces was irradiated with 3 megarads of electron beam energy from a 2 MEV electron accelerator to crosslink the copolymer.

The netting having the crosslinked copolymer on its surface was heated to a temperature above the softening point of the copolymer and then employed as an orthopedic cast forming bandage to apply a forearm-wrist cast to a subject in a manner similar to that of Example 5. The applied layers of heated bandage fused satisfactorily to form a unitary cast which was close fitting and rigid at room temperature.

What is claimed is:

1. Method of applying an orthopedic cast to a portion of a human or animal body which comprises:
   (A) heating a flexible bandage material suitable for forming an orthopedic cast, comprising a substrate in the form of a netting, the strands of said netting having on their surfaces a coating comprising a crosslinked copolymer, said crosslinked copolymer being produced by crosslinking a thermoplastic, crosslinkable copolymer which is produced by the process which comprises reacting, at a temperature from 25° to 300° C., an active-hydrogen containing initiator with a molar excess of a monomer mixture comprising:
      (i) from 80 to 99.5 weight percent of at least one lactone of the formula

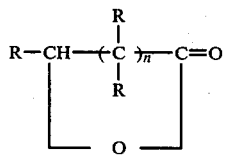

wherein n is an integer having a value from about 3 to 6, at least N+2 of the R's are hydrogen and the remaining R's are each alkyl or 1 to 10 carbon atoms; and
      (ii) from 0.5 to 99.5 weight percent of a polyfunctional acrylate monomer
   to a temperature above the softening point of the crosslinked copolymer;
   (B) wrapping the heated bandage material around the body portion in a repetitive manner to form overlying layers of bandage material conforming in shape to the body portion and forming an encasement therefor;
   (C) applying sufficient pressure during and after wrapping to the overlying layers to ensure contact which causes fusion of the overlying layers into a unitary structure encasing the body portion; and
   (D) cooling the applied layers of bandage to form a rigid, unitary structure.

2. Method as claimed in claim 1, wherein the lactone employed in producing the thermoplastic, crosslinkable copolymer is epsilon-caprolactone.

3. Method as claimed in claim 2, wherein the polyfunctional acrylate employed in producing the thermoplastic, crosslinkable copolymer is neopentyl glycol diacrylate.

4. Method as claimed in claim 1, wherein said bandage material is heated by exposing it to electromagnetic radiation in the frequency range from 500 to 5,000 $MH_z$.

5. Method of applying a splint to a portion of the human or animal body comprising:
   (A) heating a sheet of a polymeric material of $\frac{1}{8}$-inch to $\frac{1}{2}$-inch thickness, comprising a crosslinked copolymer, to a temperature above the softening point of the crosslinked copolymer being one which is produced by crosslinking a thermoplastic, crosslinkable copolymer which has been produced by reacting, at a temperature of from 25° to 300° C., an active hydrogen containing initiator with a molar excess of a monomer mixture comprising:
      (1) from 90 to 99.5 weight percent of at least one lactone of the formula

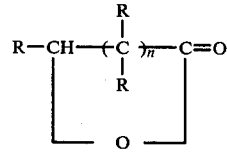

wherein n is an integer having a value of from about 3 to 6, at least n+2 of the R's are hydrogen and the remaining R's are each alkyl of 1 to 10 carbon atoms; and
      (2) from 0.5 to 10 weight percent of a polyfunctional acrylate monomer;
   (B) molding the heated sheet to conform to the surface contours of the body portion;
   (C) allowing the molded sheet to cool to a rigid state; and
   (D) affixing the molded sheet to the body portion by the application of fastening means.

6. Method as claimed in claim 5, wherein said lactone is epsilon-caprolactone.

7. Method as claimed in claim 6, wherein said polyfunctional acrylate is neopentyl glycol diacrylate.

8. Method as claimed in claim 5, wherein said lactone is present in the polymerization reaction mixture at a concentration of from 95 to 99.5 weight percent and said polyfunctional acrylate is present in the polymerization reaction mixture at a concentration of from 0.5 to 5 weight percent.

* * * * *